(12) United States Patent
Ernst et al.

(10) Patent No.: US 7,429,592 B2
(45) Date of Patent: Sep. 30, 2008

(54) CYANOANTHRANILAMIDE DERIVATIVES AND THE USE THEREOF AS MEDICAMENTS

(75) Inventors: Alexander Ernst, Berlin (DE); Andreas Huth, Berlin (DE); Martin Krueger, Berlin (DE); Karl-Heinz Thierauch, Berlin (DE); Andreas Menrad, Oranienburg (DE); Martin Haberey, Berlin (DE)

(73) Assignee: Schering Aktienegesellschaft, Berlin (DE)

( * ) Notice: Subject to any disclaimer, the term of this patent is extended or adjusted under 35 U.S.C. 154(b) by 345 days.

(21) Appl. No.: 10/476,761

(22) PCT Filed: May 3, 2002

(86) PCT No.: PCT/EP02/04921

§ 371 (c)(1),
(2), (4) Date: Aug. 25, 2004

(87) PCT Pub. No.: WO03/000678

PCT Pub. Date: Jan. 3, 2003

(65) Prior Publication Data

US 2004/0266770 A1    Dec. 30, 2004

(30) Foreign Application Priority Data

May 8, 2001    (DE) ................. 101 23 587
May 15, 2001    (DE) ................. 101 25 295

(51) Int. Cl.
*C07D 401/12* (2006.01)
*A61K 31/44* (2006.01)
*A61K 31/47* (2006.01)

(52) U.S. Cl. ............... 514/256; 514/307; 514/311; 514/357; 544/242; 546/139; 546/152; 546/329

(58) Field of Classification Search ......... 546/329; 514/357

See application file for complete search history.

(56) References Cited

U.S. PATENT DOCUMENTS

| 6,448,277 B2 | 9/2002 | Altmann et al. |
| 6,878,720 B2 | 4/2005 | Altmann et al. |
| 7,002,022 B2 | 2/2006 | Altmann et al. |
| 7,122,547 B1 | 10/2006 | Huth et al. |
| 2002/0019414 A1 | 2/2002 | Altmann et al. |

FOREIGN PATENT DOCUMENTS

| DE | 19910396 A1 | 9/2000 |
| EP | 0650961 A1 | 5/1995 |
| WO | WO 9426260 A1 | 11/1994 |
| WO | WO 0027819 | 5/2000 |
| WO | WO 0185671 | 11/2001 |
| WO | WO 02055501 | 7/2002 |

OTHER PUBLICATIONS

Wermuth et al: "The practise of Medicinal Chemistry" Practice of Medicinal Chemistry XX, XX, 1996 pp. 203-237, XP002190259.

*Primary Examiner*—Zinna N Davis
(74) *Attorney, Agent, or Firm*—Millen, White, Zelano, Branigan, P.C.

(57) ABSTRACT

Substituted cyanoanthranilamide derivatives, their production and use as pharmaceutical agents for treating diseases that are triggered by persistent angiogenesis are described. The compounds according to the invention can be used as or in the case of psoriasis, Kaposi's sarcoma, restenosis, such as, e.g., stent-induced restenosis, endometriosis, Crohn's disease, Hodgkin's disease, leukemia; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and inhibition of the reocclusion of vessels after balloon catheter treatment, in vascular prosthetics or after mechanical devices are used to keep vessels open, such as, e.g., stents, as immunosuppressive agents, as a support in scar-free healing, senile keratosis and contact dermatitis. The compounds according to the invention can also be used as VEGFR-3 inhibitors in the case of lymphangiogenesis.

10 Claims, No Drawings

CYANOANTHRANILAMIDE DERIVATIVES AND THE USE THEREOF AS MEDICAMENTS

This application is a 371 of PCT/EP02/04921 filed May 3, 2002.

The invention relates to substituted cyanoanthranilamide derivatives, their production and use as pharmaceutical agents for treating diseases that are triggered by persistent angiogenesis.

Persistent angiogenesis can be the cause of various diseases, such as psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases and arteriosclerosis or can result in an aggravation of these diseases.

Persistent angiogenesis is induced by the factor VEGF via its receptor. So that VEGF can exert this action, it is necessary that VEGF bind to the receptor, and a tyrosine phosphorylation is induced.

Direct or indirect inhibition of the VEGF receptor (VEGF=vascular endothelial growth factor) can be used for treating such diseases and other VEGF-induced pathological angiogenesis and vascular permeable conditions, such as tumor vascularization. For example, it is known that the growth of tumors can be inhibited by soluble receptors and antibodies against VEGF.

Anthranilic acid amides that are used as pharmaceutical agents for treating psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, are known from WO 00/27819.

The known compounds are generally effective in the indications cited, but their effectiveness generally accompanies inhibitory potential compared to metabolizing enzymes of the liver (Cytochrome P450 isoenzymes). This involves the danger of undesirable pharmaceutical agent interactions and thus produces an inferior compatibility of the medication.

There is therefore a desire, on the one hand, for more effective compounds, and, on the other hand, for more toxicologically harmless compounds, which, moreover, should also be more compatible.

It has now been found that compounds of general formula I

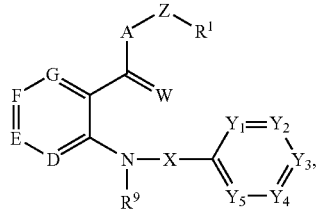

(I)

in which
A stands for the group —N(R$^7$)—,
W stands for oxygen, sulfur, two hydrogen atoms or the group —N(R$^8$)—,
Z stands for a bond, the group —N(R$^{10}$)— or =N—, for branched or unbranched $C_1$-$C_{12}$-alkyl or for the group

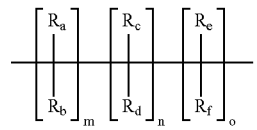

m, n and o stand for 0-3,
$R_a$, $R_b$, $R_c$, $R_d$, $R_e$, $R_f$, independently of one another, stand for hydrogen, fluorine, $C_1$-$C_4$-alkyl or the group —N(R$^{11}$)—, and/or $R_a$ and/or $R_b$ can form a bond with $R_c$ and/or $R_d$ or $R_c$ can form a bond with $R_e$ and/or $R_f$ or up to two of radicals $R_a$-$R_f$ can close a bridge with up to 3 C atoms each to form R$^1$ or to form R$^7$,
X stands for $C_1$-$C_6$-alkyl,
R$^1$ stands for branched or unbranched $C_1$-$C_{12}$-alkyl or $C_2$-$C_{12}$-alkenyl that is optionally substituted in one or more places in the same way or differently with halogen, hydroxy, $C_1$-$C_6$-alkyloxy, aralkyloxy, $C_1$-$C_6$-alkyl and/or with the group —NR$^{12}$R$^{13}$; or for $C_3$-$C_{10}$-cycloalkyl or $C_3$-$C_{10}$-cycloalkenyl that is optionally substituted in one or more places in the same way or differently with halogen, hydroxy, $C_1$-$C_6$-alkyloxy, $C_1$-$C_6$-alkyl and/or with the group —NR$^{12}$R$^{13}$; or for aryl or hetaryl that is optionally substituted in one or more places in the same way or differently with halogen, hydroxy, $C_1$-$C_6$-alkyloxy, aralkyloxy, $C_1$-$C_6$-alkyl, halo-$C_1$-$C_6$-alkyl, cyano-$C_1$-$C_6$-alkyl or with the group =O, OR$^{14}$, or R$^{14}$,
$Y_1$ to $Y_5$ in each case stand for a nitrogen atom or for the group —CY$^6$,
Y$^6$ stands for cyano, halogen, $C_1$-$C_6$-alkyl, $C_1$-$C_6$-alkoxy, amino or hydroxy, whereby at least one nitrogen atom is contained in the ring and at least one cyano radical is contained on the ring,
D stands for a nitrogen atom or for the group C—R$^3$,
E stands for a nitrogen atom or for the group C—R$^4$,
F stands for a nitrogen atom or for the group C—R$^5$,
G stands for a nitrogen atom or for the group C—R$^6$, whereby
R$^3$, R$^4$, R$^5$ and R$^6$ stand for hydrogen, halogen, or $C_1$-$C_6$-alkoxy, $C_1$-$C_6$-alkyl or $C_1$-$C_6$-carboxyalkyl that is unsubstituted or that is optionally substituted in one or more places with halogen,
R$^7$ stands for hydrogen or $C_1$-$C_6$-alkyl or forms a bridge with up to 3 ring members with $R_a$-$R_f$ from Z or to form R$^1$,
R$^8$, R$^9$, R$^{10}$ and R$^{11}$ stand for hydrogen or $C_1$-$C_6$-alkyl,
R$^{12}$ and R$^{13}$ stand for hydrogen, $C_1$-$C_6$-alkyl or form a ring that can contain another heteroatom,
R$^{14}$ stands for the group $C_1$-$C_{15}$-alkyl-R$^{15}$, in which the alkyl radical can be interrupted in one or more places by oxygen, or for the group $(CH_2—CH_2—O)_u(CH_2)_v—R^{15}$,
R$^{15}$ stands for aryl, hetaryl, $C_1$-$C_6$-alkyl, aralkyl, —CH$_2$CN or for the group NR$^{16}$R$^{17}$,
R$^{16}$ and R$^{17}$ stand for hydrogen, $C_1$-$C_6$-alkyl, $C_1$-$C_6$-acyl or form a ring that can contain another heteroatom,
u and v stand for 0-5, as well as isomers, enantiomers and salts thereof that overcome the above-indicated drawbacks.

The compounds according to the invention prevent a tyrosine phosphorylation or stop persistent angiogenesis and thus the growth and propagation of tumors, whereby they are distinguished in particular by a slighter inhibition of isoforms of Cytochrome P 450 (2C9 and 2C19). The medication with the compounds according to the invention can therefore be carried out risk-free without regard to accompanying administered pharmaceutical agents that are degraded by these isoforms.

If $R^7$ forms a bridge to $R^1$, heterocyclic compounds result to which $R^1$ is fused. For example, there can be mentioned:

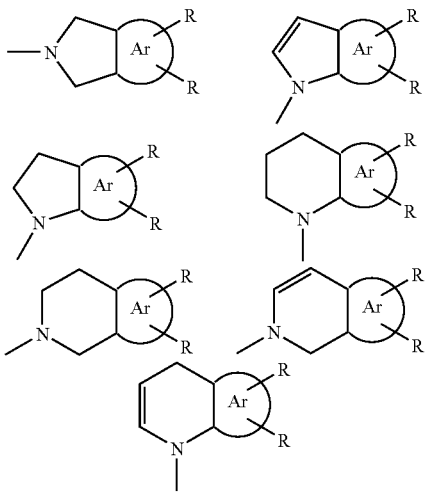

If $R_a$, $R_b$, $R_c$, $R_d$, $R_e$, $R_f$ independently of one another, represent hydrogen or $C_1$-$C_4$ alkyl, Z thus forms an alkyl chain.

If $R_a$ and/or $R_b$ form a bond with $R_c$ and/or $R_d$, or $R_c$ and/or $R_d$ form a bond with $R_e$ and/or $R_f$, Z stands for an alkenyl or alkinyl chain.

If $R_a$-$R_f$ form a bridge on their own, Z represents a cycloalkyl group or a cycloalkenyl group.

If up to two of radicals $R_a$-$R_f$ form a bridge with up to 3 C atoms to form $R^1$, Z together with $R^1$ is a benzocondensed or hetaryl-condensed (Ar) cycloalkyl. For example, there can be mentioned:

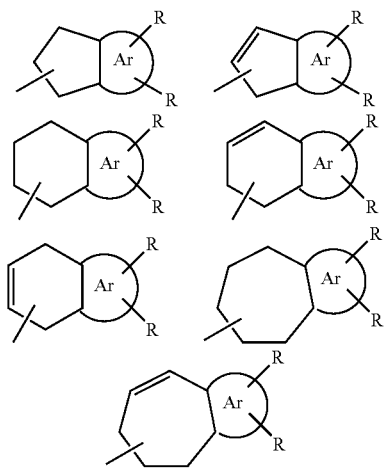

If one of radicals $R_a$-$R_f$ closes a bridge to form $R^7$, a nitrogen heterocyclic compound is formed that can be separated from $R^1$ by a group. For example, there can be mentioned:

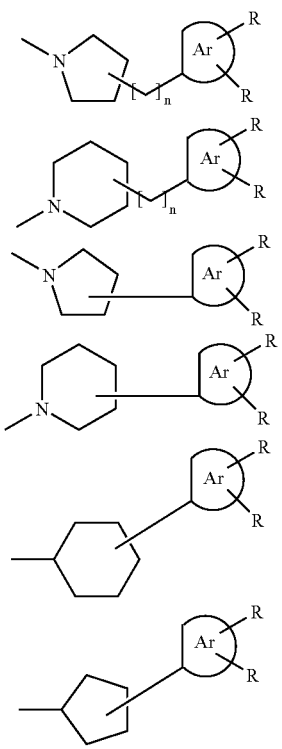

Alkyl is defined in each case as a straight-chain or branched alkyl radical, such as, for example, methyl, ethyl, propyl, isopropyl, butyl, isobutyl, sec-butyl, pentyl, isopentyl, or hexyl, heptyl, octyl, nonyl, decyl, undecyl, or dodecyl.

Alkoxy is defined in each case as a straight-chain or branched alkoxy radical, such as, for example, methyloxy, ethyloxy, propyloxy, isopropyloxy, butyloxy, isobutyloxy, sec-butyloxy, pentyloxy, isopentyloxy, hexyloxy, heptyloxy, octyloxy, nonyloxy, decyloxy, undecyloxy or dodecyloxy.

Cycloalkyls are defined as monocyclic alkyl rings, such as cyclopropyl, cyclobutyl, cyclopentyl, cyclohexyl, or cycloheptyl, cyclooctyl, cyclononyl or cyclodecyl, but also bicyclic rings or tricyclic rings, such as, for example, adamantanyl.

Cycloalkenyl is defined in each case as cyclobutenyl, cyclopentenyl, cyclohexenyl, cycloheptenyl, cyclooctenyl, cyclononenyl or cyclodecenyl, whereby the linkage can be carried out both to the double bond and to the single bonds.

Halogen is defined in each case as fluorine, chlorine, bromine or iodine.

Alkenyl is defined in each case as a straight-chain or branched alkenyl radical that contains 2-6, preferably 2-4, C atoms. For example, the following radicals can be mentioned: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, but-3-en-1-yl, and allyl.

The aryl radical in each case has 6-12 carbon atoms, such as, for example, naphthyl, biphenyl and especially phenyl.

The heteroaryl radical in each case comprises 3-16 ring atoms, and instead of the carbon can contain one or more heteroatoms that are the same or different, such as oxygen, nitrogen or sulfur, in the ring, and can be monocyclic, bicyclic, or tricyclic, and in addition in each case can be benzocondensed.

For example, there can be mentioned:

Thienyl, furanyl, pyrrolyl, oxazolyl, thiazolyl, imidazolyl, pyrazolyl, isoxazolyl, isothiazolyl, oxadiazolyl, triazolyl, thiadiazolyl, etc., and benzo derivatives thereof, such as, e.g., benzofuranyl, benzothienyl, benzoxazolyl, benzimidazolyl, indazolyl, indolyl, isoindolyl, etc.; or pyridyl, pyridazinyl, pyrimidinyl, pyrazinyl, triazinyl, etc., and benzo derivatives thereof, such as, e.g., quinolyl, isoquinolyl, etc.; azocinyl, indolizinyl, benzimidazolyl, purinyl, etc., and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, or oxepinyl, etc.

The aryl radical and the heteroaryl radical in each case can be substituted in the same way or differently in 1, 2 or 3 places with hydroxy, halogen, $C_1$-$C_4$-alkoxy, with $C_1$-$C_4$-alkyl or $C_1$-$C_4$-alkyl that is substituted in one or more places with halogen.

If an acid group is included, the physiologically compatible salts of organic and inorganic bases are suitable as salts, such as, for example, the readily soluble alkali salts and alkaline-earth salts as well as N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropanediol, Sovak base, and 1-amino-2,3,4-butanetriol.

If a basic group is included, the physiologically compatible salts of organic and inorganic acids are suitable, such as hydrochloric acid, sulfuric acid, phosphoric acid, citric acid, tartaric acid, fumaric acid, i.a.

The compounds of general formula I according to the invention also contain the possible tautomeric forms and comprise the E-isomers or Z-isomers, or, if a chiral center is present, also the racemates and enantiomers.

Those compounds of general formula I in which

A stands for the group —$N(R^7)$—,

W stands for oxygen,

Z stands for a bond or for branched or unbranched $C_1$-$C_{12}$-alkyl,

X stands for $C_1$-$C_6$-alkyl, $R^1$ stands for branched or unbranched $C_1$-$C_{12}$-alkyl or $C_2$-$C_{12}$-alkenyl that is optionally substituted in one or more places in the same way or differently with halogen, hydroxy, $C_1$-$C_6$-alkyloxy, aralkyloxy, $C_1$-$C_6$-alkyl and/or with the group —$NR^{12}R^{13}$; or for $C_3$-$C_{10}$-cycloalkyl or $C_3$-$C_{10}$-cycloalkenyl that is optionally substituted in one or more places in the same way or differently with halogen, hydroxy, $C_1$-$C_6$-alkyloxy, $C_1$-$C_6$-alkyl and/or with the group —$NR^{12}R^{13}$; or for aryl or hetaryl that is optionally substituted in one or more places in the same way or differently with halogen, hydroxy, $C_1$-$C_6$-alkyloxy, aralkyloxy, $C_1$-$C_6$-alkyl, halo-$C_1$-$C_6$-alkyl, cyano-$C_1$-$C_6$-alkyl or with the group =O, $OR^{14}$, or $R^{14}$, $Y_1$ to $Y_5$ in each case stand for a nitrogen atom or for the group —$CY^6$, $Y^6$ stands for cyano, halogen, $C_1$-$C_6$-alkyl, $C_1$-$C_6$-alkoxy, amino or hydroxy, whereby at least one nitrogen atom is contained in the ring and at least one cyano radical is contained on the ring, D stands for a nitrogen atom or for the group C—$R^3$, E stands for a nitrogen atom or for the group C—$R^4$, F stands for a nitrogen atom or for the group C—$R^5$, G stands for a nitrogen atom or for the group C—$R^6$, whereby $R^3$, $R^4$, $R^5$ and $R^6$ stand for hydrogen, halogen, or for $C_1$-$C_6$-alkoxy, $C_1$-$C_6$-alkyl or $C_1$-$C_6$-carboxyalkyl that is unsubstituted or that is optionally substituted in one or more places with halogen, $R^7$ stands for hydrogen or $C_1$-$C_6$-alkyl, or forms a bridge with up to 3 ring members with $R_a$-$R_f$ from Z or to form $R^1$, $R^9$ stands for hydrogen or $C_1$-$C_6$-alkyl, $R^{12}$ and $R^{13}$ stand for hydrogen, $C_1$-$C_6$-alkyl or form a ring that can contain another heteroatom, $R^{14}$ stands for the group $(CH_2$—$CH_2$—$O)_u(CH_2)_v$—$R^{15}$, $R^{15}$ stands for aryl, hetaryl, $C_{1-6}$-alkyl, aralkyl, —$CH_2CN$ or for the group $NR^{16}R^{17}$, $R^{16}$ and $R^{17}$ stand for hydrogen, $C_1$-$C_6$-alkyl, $C_1$-$C_6$-acyl or form a ring that can contain another heteroatom, and u and v stand for 0-5, as well as isomers, enantiomers and salts thereof, have proven especially effective.

Those compounds of general formula I in which

A stands for the group —$N(R^7)$—,

W stands for oxygen,

Z stands for a bond or for branched or unbranched $C_1$-$C_{12}$-alkyl,

X stands for $C_1$-$C_6$-alkyl, $R^1$ stands for aryl or hetaryl that is optionally substituted in one or more places in the same way or differently with halogen, hydroxy, $C_1$-$C_6$-alkyloxy, aralkyloxy, $C_1$-$C_6$-alkyl, halo-$C_1$-$C_6$-alkyl, cyano-$C_1$-$C_6$-alkyl or with the group =O, $OR^{14}$, or $R^{14}$, $Y_1$ to $Y_5$ together stand for a pyridyl ring, which is substituted with a cyano group and which in addition can be substituted with halogen, $C_1$-$C_6$-alkyl, $C_1$-$C_6$-alkoxy, amino, $C_1$-$C_6$-carboxyalkylamino or hydroxy, D stands for a nitrogen atom or for the group C—$R^3$, E stands for a nitrogen atom or for the group C—$R^4$, F stands for a nitrogen atom or for the group C—$R^5$, G stands for a nitrogen atom or for the group C—$R^6$, whereby $R^3$, $R^4$, $R^5$ and $R^6$ stand for hydrogen, halogen or $C_1$-$C_6$-alkoxy, $C_1$-$C_6$-alkyl or $C_1$-$C_6$-carboxyalkyl that is unsubstituted or that is optionally substituted in one or more places with halogen, $R^7$ stands for hydrogen or $C_1$-$C_6$-alkyl or forms a bridge with up to 3 ring members with $R_a$-$R_f$ from Z or to form $R^1$, $R^9$ stands for hydrogen or $C_1$-$C_6$-alkyl, $R^{14}$ stands for the group $(CH_2$—$CH_2$—$O)_u(CH_2)_v$—$R^{15}$, $R^{15}$ stands for aryl, hetaryl, $C_{1-6}$-alkyl, aralkyl, —$CH_2CN$ or for the group $NR^{16}R^{17}$, $R^{16}$ and $R^{17}$ stand for hydrogen, $C_1$-$C_6$-alkyl, $C_1$-$C_6$-acyl or form a ring that can contain another heteroatom, and u and v stand for 0-5, as well as isomers, enantiomers and salts thereof, are especially effective.

Those compounds of general formula I in which

A stands for the group —$N(R^7)$—,

W stands for oxygen,

Z stands for a bond or $C_1$-$C_6$-alkyl,

X stands for $C_1$-$C_6$-alkyl, $R^1$ stands for thiophene, furan, oxazole, thiazole, indazolyl, imidazole, pyrazole, pyridine, pyrimidine, triazine, quinoline, isoquinoline or

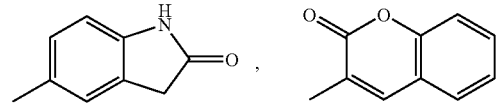

oder [or]

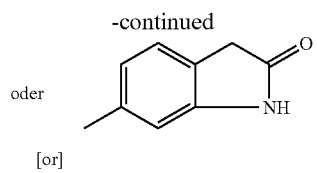

that is optionally substituted in one or more places in the same way or differently with halogen, hydroxy, $C_1$-$C_6$-alkyloxy, aralkyloxy, $C_1$-$C_6$-alkyl, halo-$C_1$-$C_6$-alkyl, cyano-$C_1$-$C_6$-alkyl or with the group =O, $Y_1$ to $Y_5$ together stand for a pyridyl ring, which is substituted with a cyano group and which in addition can be substituted with halogen, D stands for a nitrogen atom or for the group C—$R^3$,
E stands for the group C—$R^4$,
F stands for the group C—$R^5$,
G stands for the group C—$R^6$, whereby
$R^3$, $R^4$, $R^5$ and $R^6$ stand for hydrogen,
$R^7$ stands for hydrogen, and
$R^9$ stands for hydrogen, as well as isomers, enantiomers, and salts thereof, are quite especially effective.

Those compounds of general formula I in which
A stands for the group —N($R^7$)—,
W stands for oxygen,
Z stands for a bond,
X stands for $C_1$-$C_6$-alkyl,
$R^1$ stands for indazolyl, quinoline, isoquinoline or

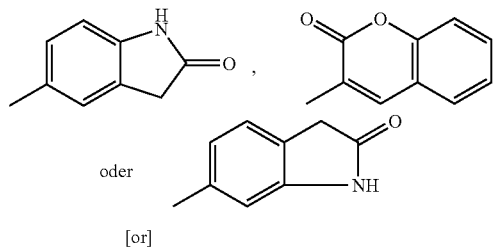

oder [or]

that is optionally substituted in one or more places in the same way or differently with $C_1$-$C_6$-alkyloxy, $C_1$-$C_6$-alkyl, cyano-$C_1$-$C_6$-alkyl or with the group =O, $Y_1$ to $Y_5$ together stand for a pyridyl ring, which is substituted with a cyano group and which in addition can be substituted with halogen, D stands for a nitrogen atom or for the group C—$R^3$,
E stands for the group C—$R^4$,
F stands for the group C—$R^5$,
G stands for the group C—$R^6$, whereby
$R^3$, $R^4$, $R^5$ and $R^6$ stand for hydrogen,
$R^7$ stands for hydrogen, and
$R^9$ stands for hydrogen, as well as isomers, enantiomers, and salts thereof, are also quite especially effective.

The compounds of formula I as well as their physiologically compatible salts can be used as pharmaceutical agents based on their inhibitory activity relative to the phosphorylation of the VEGF receptor. Based on their profile of action, the compounds according to the invention are suitable for treating diseases that are caused or promoted by persistent angiogenesis.

Since the compounds of formula I are identified as inhibitors of the tyrosine kinases KDR and FLT, they are suitable in particular for treating those diseases that are caused by persistent angiogenesis that is triggered via the VEGF receptor or caused or promoted by an increase in vascular permeability.

The subject of this invention is also the use of the compounds according to the invention as inhibitors of the tyrosine kinases KDR and FLT.

Subjects of this invention are thus also pharmaceutical agents for treating tumors or use thereof.

The compounds according to the invention can be used either alone or in a formulation as pharmaceutical agents for treating psoriasis, Kaposi's sarcoma, restenosis, such as, e.g., stent-induced restenosis, endometriosis, Crohn's disease, Hodgkin's disease, leukemia; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, as immunosuppressive agents, for supporting scar-free healing, in senile keratosis and in contact dermatitis.

In treating injuries to nerve tissue, quick scar formation on the injury sites can be prevented with the compounds according to the invention, i.e., scar formation is prevented from occurring before the axons reconnect. A reconstruction of the nerve compounds was thus facilitated.

The formation of ascites in patients can also be suppressed with the compounds according to the invention. VEGF-induced edemas can also be suppressed.

Lymphangiogenesis plays an important role in lymphogenic metastasizing (Karpanen, T. et al., Cancere Res. 2001 Mar. 1, 61(5): 1786-90, Veikkola, T., et al., EMBO J. 2001, Mar. 15; 20(6): 1223-31).

The compounds according to the invention now also show excellent action as VEGFR kinase 3 inhibitors and are therefore also suitable as effective inhibitors of lymphangiogenesis.

By a treatment with the compounds according to the invention, not only a reduction of the size of metastases but also a reduction of the number of metastases is achieved.

Such pharmaceutical agents, their formulations and uses, are also subjects of this invention.

The invention thus also relates to the use of the compounds of general formula I for the production of a pharmaceutical agent for use as or for treatment of psoriasis, Kaposi's sarcoma, restenosis, such as, e.g., stent-induced restenosis, endometriosis, Crohn's disease, Hodgkin's disease, leukemia; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, as immunosuppressive agents, for supporting scar-free healing, in senile keratosis and in contact dermatitis.

The formation of ascites in patients can also be suppressed with the compounds according to the invention. VEGF-induced edemas can also be suppressed.

To use the compounds of formula I as pharmaceutical agents, the latter are brought into the form of a pharmaceutical preparation, which in addition to the active ingredient for enteral or parenteral administration contains suitable pharmaceutical, organic or inorganic inert carrier materials, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, capsules, or in liquid form, for example as solutions, suspensions or emulsions. They also contain, moreover, adjuvants such as preservatives, stabilizers, wetting agents or emulsifiers, salts for changing osmotic pressure or buffers.

For parenteral administration, especially injection solutions or suspensions, especially aqueous solutions of the active compounds in polyhydroxyethoxylated castor oil, are suitable.

As carrier systems, surface-active adjuvants such as salts of bile acids or animal or plant phospholipids, but also mixtures thereof as well as liposomes or components thereof can also be used.

For oral administration, especially tablets, coated tablets or capsules with talc and/or hydrocarbon vehicles or binders, such as for example, lactose, corn starch or potato starch, are suitable. The administration can also be carried out in liquid form, such as, for example, as juice, to which optionally a sweetener or, if necessary, one or more flavoring substances, is added.

The dosage of the active ingredients can vary depending on the method of administration, age and weight of the patient, type and severity of the disease to be treated and similar factors. The daily dose is 0.5-1000 mg, preferably 50-200 mg, whereby the dose can be given as a single dose to be administered once or divided into 2 or more daily doses.

The above-described formulations and forms for dispensing are also subjects of this invention.

The production of the compounds according to the invention is carried out according to methods that are known in the art. For example, compounds of formula I are obtained, in that a) in a compound of general formula II

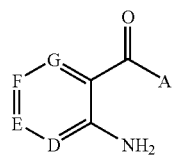

in which D to G have the meanings that are indicated in general formula I and A stands for the group $OR^{13}$, whereby $R^{13}$ stands for hydrogen, $C_{1-4}$-alkyl or $C_{1-6}$-acyl, first the amine group is alkylated, and then COA is converted into an amide; or the $NH_2$ group is converted into halogen, A is converted into an amide, and halogen is converted into the corresponding amine and optionally a protective group is cleaved off and a halogen is converted into cyanide or an N-oxide is converted into a nitrile, or b) a compound of general formula III

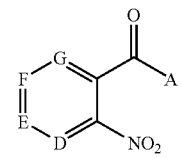

in which D to G have the meanings that are indicated in general formula I and A stands for halogen or the group $OR^{13}$, whereby hydrogen, $C_{1-6}$-alkyl or $C_{1-6}$-acyl stands for $R^{13}$, COA is converted into an amide, the nitro group is reduced to amine and then alkylated, and optionally a heterocyclic compound is converted into an N-oxide, or c) a compound of general formula IV

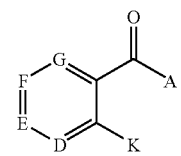

in which D to G have the meanings that are indicated in general formula I, and K stands for hydroxy or halogen, and A stands for halogen or for the group $OR^{13}$, whereby $R^{13}$ can stand for hydrogen, $C_{1-6}$-alkyl, or $C_{1-6}$-acyl, K is converted into an amine, COA is converted into an amide, if K stands for hydroxy, it is converted into halogen, and then the process is continued as above, or d) a compound of general formula V is first alkylated and then the anhydride is converted into the amide.

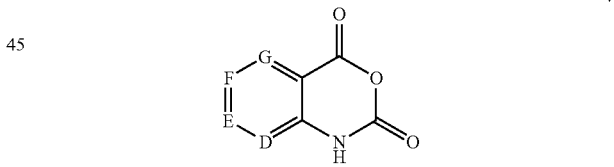

The sequence of process steps can be interchanged in all cases.

The amide formation is carried out according to methods that are known in the literature.

For amide formation, it is possible to start from a corresponding ester. The ester is reacted according to J. Org. Chem. 1995, 8414 with aluminum trimethyl and the corresponding amine in solvents such as toluene at temperatures of 0° C. to the boiling point of the solvent. If the molecule contains two ester groups, both are converted into the same amide.

When nitrites are used instead of ester, amidines are obtained under analogous conditions.

For amide formation, however, all processes that are known from peptide chemistry are also available. For example, the corresponding acid can be reacted with the amine in aprotic polar solvents, such as, for example, dimethylformamide, via an activated acid derivative, obtainable, for example, with hydroxybenzotriazole and a carbodiimide, such as, for example, diisopropylcarbodiimide, or else with preformed reagents, such as, for example, HATU (Chem. Comm. 1994, 201) or BTU, at temperatures of between 0° C. and the boiling point of the solvent. For the amide formation, the process can also be used with the mixed acid anhydride, the acid chloride, the imidazolide or the azide. With reactions of the acid chloride, dimethylacetamide is preferred as solvent at temperatures from room temperature up to the boiling point of the solvent, preferably at 80-100° C.

If various amide groups are to be introduced into the molecule, for example the second ester group must be introduced into the molecule after the production of the first amide group and then amidated, or there is a molecule in which one group is present as an ester, the other is present as an acid, and the two groups are amidated in succession according to various methods.

Thioamides can be obtained from the anthranilamides by reaction with diphosphadithianes according to Bull Soc. Chim. Belg. 87, 229, 1978 or by reaction with phosphorus pentasulfide in solvents such as pyridine or even quite without solvent at temperatures of 0° C. to 200° C.

The reduction of the nitro group is performed in polar solvents at room temperature or elevated temperature. As catalysts for the reduction, metals such as Raney nickel or noble-metal catalysts such as palladium or platinum or else palladium hydroxide optionally on vehicles are suitable. Instead of hydrogen, for example, ammonium formate, cyclohexene or hydrazine can also be used in a known way. Reducing agents such as tin(II) chloride or titanium(III) chloride can also be used, such as complex metal hydrides, optionally in the presence of heavy metal salts. Iron can also be used as a reducing agent. The reaction is then performed in the presence of an acid, such as, e.g., acetic acid or ammonium chloride, optionally with the addition of a solvent, such as, for example, water, methanol, iron/ammonia, etc. With an extended reaction time, an acylation of the amino group can occur in this variant.

If an alkylation of an amino group is desired, the amine can be subjected to reductive alkylation with aldehydes or ketones, whereby the reaction is performed in the presence of a reducing agent, such as, for example, sodium cyanoborohydride in a suitable inert solvent, such as, for example, ethanol, at temperatures of 0° C. up to the boiling point of the solvent. If a start is made from a primary amino group, the reaction can be performed optionally in succession with two different carbonyl compounds, whereby mixed derivatives are obtained [Literature, e.g., Verardo et al. Synthesis (1993), 121; Synthesis (1991), 447; Kawaguchi, Synthesis (1985), 701; Micovic et al. Synthesis (1991), 1043]. It can be advantageous first to form the Schiff base by reaction of the aldehyde with the amine in solvents such as ethanol or methanol, optionally with the addition of adjuvants such as glacial acetic acid, and then to add only reducing agents, such as, e.g., sodium cyanoborohydride. An N-oxide withstands these reaction conditions.

An alkylation thus also can be achieved in that the reaction is performed according to the Mitsonubo variant with an alcohol in the presence of, for example, triphenylphosphine and azodicarboxylic acid ester. An alkylation of the amino group can also be carried out, however, by alkylating agents such as halides, tosylates, mesylates or triflates. As solvents, for example, polar solvents such as ethanol, tetrahydrofuran, acetonitrile or dimethylformamide are suitable. The addition of an auxiliary base such as triethylamine, DABCO pyridine or potassium carbonate can be advantageous.

Since the danger of a double alkylation exists in the case of a free amino group, isatoic acid anhydride can advantageously be used. With bases such as sodium hydride or else cesium carbonate in solvents such as tetrahydrofuran or dimethylformamide at temperatures of between room temperature and the boiling point of the solvent, preferably at 60° C., it can be converted into the anion that is then further reacted with the alkylating agent.

Ether cleavages are performed according to processes that are common in the literature. In this case, a selective cleavage can be achieved even in the case of several groups that are present in the molecule. In this case, the ether is treated with, for example, boron tribromide in solvents such as dichloromethane at temperatures of between −100° C. up to the boiling point of the solvent, preferably at −78° C. It is also possible, however, to cleave the ether by sodium thiomethylate in solvents such as dimethylformamide. The temperature can be between room temperature and the boiling point of the solvent, preferably at 150° C. In the case of benzyl ethers, the cleavage can also be accomplished with strong acids, such as, for example, trifluoroacetic acid at temperatures from room temperature to boiling point.

The conversion of a hydroxy group, which is in ortho-position or para-position in a nitrogen of a 6-ring hetaryl, into halogen can be performed, for example, by reaction with inorganic acid halides, such as, for example, phosphorus oxychloride, optionally in an inert solvent, at temperatures up to the boiling point of the solvent or the acid halide.

The substitution of a halogen, tosylate, triflate or nonaflate, which is in ortho-position or para-position in a nitrogen in a 6-membered heteroaromatic compound, can be accomplished by reaction with a corresponding amine in inert solvents, such as, for example, xylene, or in polar solvents, such as N-methylpyrrolidone or dimethylacetamide at temperatures of 60-170° C. Heating is also possible without solvent, however. The addition of an auxiliary base such as potassium carbonate or cesium carbonate or the addition of copper and/or copper oxide can be advantageous. In the case of non-activated halogens or triflates, a palladium-catalyzed introduction of the amine portion is possible according to J. Org. Chem. 2000, 1158. As a base, preferably sodium-t-butylate is used; as an auxiliary ligand, a biphenylphosphine is used.

The introduction of the halogens chlorine, bromine or iodine via an amino group can be carried out, for example, also according to Sandmeyer by the diazonium salts that are intermediately formed with nitrites being reacted with copper (I) chloride or copper(I) bromide in the presence of the corresponding acid, such as hydrochloric acid or hydrobromic acid or with potassium iodide.

If an organic nitrite is used, the halogens can be introduced into a solvent, such as, for example, dimethylformamide, e.g., by adding methylene iodide or tetrabromomethane. The removal of the amino group can be achieved either by reaction with an organic nitrite in tetrahydrofuran or by diazotization and reductive boiling-down of the diazonium salt with, for example, phosphorous acid, optionally with the addition of copper(I) oxide.

The introduction of fluorine can be accomplished, for example, by Balz-Schiemann reaction of the diazonium tetrafluoroborate or according to J. Fluor. Chem. 76, 1996, 59-62 by diazotization in the presence of HFxpyridine and subsequent boiling-down optionally in the presence of a fluoride ion source, such as, e.g., tetrabutylammonium fluoride.

The cleavage of the t-butoxycarbonyl group is carried out, of course, in that in a solvent such as tetrahydrofuran, dioxane or ethanol, the reaction is performed with an acid such as, e.g., 1N hydrochloric acid at temperatures of between room temperature and the boiling point of the solvent. It is also possible to cleave the t-BOC group with strong acids, such as trifluoroacetic acid, at temperatures of between −20° C. up to the boiling point, preferably at room temperature. A solvent such as methylene chloride is not absolutely necessary but can be advantageous.

The acylation of an amine is carried out in a known way, either according to the process that is described under amide formation or by reaction with activated acid derivatives, such as, for example, acid chloride or acid anhydride in solvents such as methylene chloride, acetonitrile or tetrahydrofuran, optionally in the presence of bases such as triethylamine. An addition of catalytic amounts of dimethylaminopyridine can be advantageous.

The introduction of a nitrile group is carried out according to methods that are known in the literature. Leaving groups such as halogens, tosylates, mesylates or triflates can be replaced with nitrile by heavy-metal-catalyzed reaction. As catalysts, palladium (O) or palladium(II) catalysts are suitable. As a cyanide source, for example, zinc(II) cyanide is used. As solvents, for example, dimethylacetamide or dimethylformamide is used. Additions of zinc powder and bis(diphenylphosphino)ferrocene are advantageous for the reaction. Copper(I) cyanide can also be used. As solvents, for example, dipolar aprotic solvents such as dimethylformamide are suitable.

The isomer mixtures can be separated into enantiomers or E/Z isomers according to commonly used methods, such as, for example, crystallization, any form of chromatography or salt formation.

The production of the salts is carried out in the usual way by a solution of the compound of formula I being mixed with the equivalent amount or an excess of a base or acid, which optionally is in solution, and the precipitate being separated or the solution being worked up in the usual way.

The following examples explain the production of the compounds according to the invention without the scope of the claimed compounds being limited to these examples.

EXAMPLE 1

Production of N-(Isoquinolin-3-yl)-2-(4-(2-cyanopyridylmethyl)aminobenzoic Acid Amide

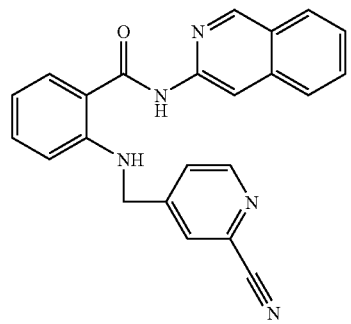

920 mg (2.5 mmol) of N-(isoquinolin-3-yl)-2-(4-pyridylmethyl)aminobenzoic acid amide-N-oxide is mixed in a glass pressure vessel in succession with 20 ml of dimethylformamide, in succession with 760 mg (7.5 mmol) of triethylamine and 1.24 g (12.5 mmol) of trimethylsilyl cyanide, and then it is heated for 10 hours to a bath temperature of 110° C. It is then diluted with water to about 200 ml and shaken out three times with 50 ml of ethyl acetate each. The collected organic phase is washed with 50 ml of water, dried, filtered and concentrated by evaporation. The residue is chromatographed first on silica gel with ethyl acetate:hexane=1:1 and then chromatographed again on silica gel with dichloromethane:ethanol=100:2 as eluant. 132 mg (14% of theory) of N-(isoquinolin-3-yl)-2-(4-2-cyanopyridylmethyl)aminobenzoic acid amide is obtained as a resin.

Similarly produced are also the following compounds:

D stands for the group C—$R^3$
E stands for the group C—$R^4$
F stands for the group C—$R^5$
G stands for the group C—$R^6$
and $R^3$, $R^4$, $R^5$ and $R^6$ in each case stand for hydrogen.

| Example No. | —Z—$R^1$ | Q | X | Melting Point [° C.] |
|---|---|---|---|---|
| 2 | | 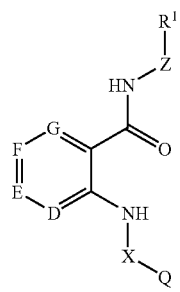 | —$CH_2$— | 173.8 |

-continued

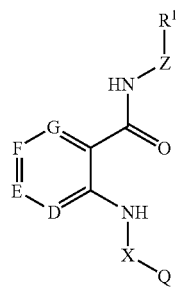

D stands for the group C—R³
E stands for the group C—R⁴
F stands for the group C—R⁵
G stands for the group C—R⁶
and R³, R⁴, R⁵ and R⁶ in each case stand for hydrogen.

| Example No. | —Z—R¹ | Q | X | Melting Point [° C.] |
|---|---|---|---|---|
| 3 | 3-methylisoquinoline | 2-cyano-3-methylpyridine | —CH₂— | 233.4 (dec.) |
| 4 | 5-methyl-2-oxoindoline | 5-methyl-2-cyanopyridine | —CH₂— | |
| 5 | 6-methyl-1-(cyanomethyl)indazole | 4-methyl-2-cyanopyridine | —CH₂— | MS: 407 (M⁺) |
| 6 | 7-methoxy-3-methylcoumarin | 5-methyl-2-cyanopyridine | —CH₂— | 173.4 |
| 7 | 6-methyl-2-oxoindoline | 5-methyl-2-cyanopyridine | —CH₂— | |
| 8 | 5-methyl-2-oxoindoline | 5-methyl-2-cyanopyridine | —CH₂— | |
| 9 | 7-methoxy-2,3-dimethylquinoline | 5-methyl-2-cyanopyridine | —CH₂— | MS: 423 (M⁺) |
| 10 | 1,6-dimethylindazole | 4-methyl-2-cyanopyridine | —CH₂— | 155-158 |
| 11 | 7-methoxy-3-methylcoumarin | 4-methyl-2-cyanopyridine | —CH₂— | 165-167 |

-continued

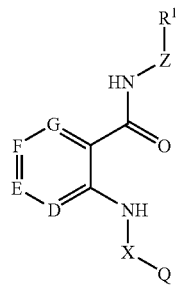

D stands for the group C—R³
E stands for the group C—R⁴
F stands for the group C—R⁵
G stands for the group C—R⁶
and R³, R⁴, R⁵ and R⁶ in each case stand for hydrogen.

| Example No. | —Z—R¹ | Q | X | Melting Point [° C.] |
|---|---|---|---|---|
| 12 | H₃C-substituted 2-methyl-7-methoxyquinoline | 4-methyl-2-cyanopyridine | —CH₂— | 153-155 |
| 13 | 6-methyl-oxindole (2-oxo-indoline) | 4-methyl-2-cyanopyridine | —CH₂— | ¹H-NMR (300MHz) D₆DMSO: δ=3.43 ppm (s, 2H), 4.57 ppm (d, 7Hz, 2H), 6.51 ppm(d, 7.5Hz, 1H), 6.68 ppm(t, 7.5Hz, 1H), 7.15 ppm(d, 7.5Hz, 1H), 7.19-7.33(m, 2H), 7.47(mc, 1H), 7.60-7.73 ppm (m, 2H), 7.89(t, 6.5Hz, 1H), 7.98 ppm(s, 1H), 8.68 ppm(d, 5.5Hz, 1H), 10.16 ppm (s, 1H), 10, 10.45 ppm(s, 1H) |
| 14 | 6-methyl-1H-indazole | 4-methyl-2-cyanopyridine | —CH₂— | ¹H-NMR (300MHz) D₆DMSO: δ=4.58 ppm (mc, 2H), 6.49-6.58 ppm(mc, 1H), 6.69 ppm(t, 7.5Hz, 1H), 7.24 ppm (mc, 1H), 7.52 ppm(d, 8Hz, 1H), 7.56-7.78 ppm(m, 3H), 7.98 ppm(mc, 2H), 8.05 ppm(s, 1H), 8.21 ppm(mc, 1H), 8.68 ppm(d, 5.5Hz, 1H), 10.22 ppm(s, 1H), 13.03 ppm s-br, 1H) |
| 15 | 2,6-dimethyl-2H-indazole | 4-methyl-2-cyanopyridine | —CH₂— | MS(EI, 4.18e6): 382 (M⁺, 27.6%), 236(M-HNC₈H₇N₂⁺, 27.6%), 147 (H₂NC₈H₇N₂⁺, 100%) |

-continued

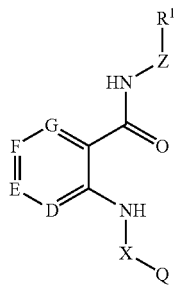

D stands for the group C—R³
E stands for the group C—R⁴
F stands for the group C—R⁵
G stands for the group C—R⁶
and R³, R⁴, R⁵ and R⁶ in each case stand for hydrogen.

| Example No. | —Z—R¹ | Q | X | Melting Point [° C.] |
|---|---|---|---|---|
| 16 | (6-methyl-1H-indazol-5-yl) | 4-methyl-2-cyanopyridin-6-yl (CN) | —CH₂— | MS(EI, 4.18e6): 368 (M⁺, 17.8%), 236(M-HNC₇H₅N₂⁺, 70.1%), 133 (H₂NC₇H₅N₂⁺, 100%) |
| 17 | 3-methylisoquinolin-4-yl | 6-bromo-4-methyl-2-cyanopyridin-yl (CN, Br) | —CH₂— | 181.0 |
| 18 | 3-methylisoquinolin-4-yl | 4-methyl-2-cyanopyridin-6-yl (CN) | —CH₂— | MS: 380 (M⁺) |

If the production of the intermediate compounds is not described, the latter are known or can be produced analogously to the known compounds or the processes that are described here.

The sample applications below explain the biological action and the use of the compounds according to the invention without the latter being limited to the examples.

Solutions Required for the Tests

Stock Solutions
Stock solution A: 3 mmol of ATP in water, pH 7.0 (−70° C.)
Stock solution B: g-33P-ATP 1 mCi/100 μl
Stock solution C: poly-(Glu4 Tyr) 10 mg/ml in water Solution for Dilutions
Substrate solvent: 10 mmol of DTT, 10 mmol of manganese chloride, 100 mmol of magnesium chloride
Enzyme solution: 120 mmol of tris/HCl, pH 7.5, 10 pM of sodium vanadium oxide Sample Application 1

Inhibition of the KDR- and FLT-1 Kinase Activity in the Presence of the Compounds According to the Invention In a microtiter plate (without protein binding) that tapers to a point, 10 μl of substrate mix (10 μl of volume of ATP stock solution A+25 μCi of g-33P-ATP (about 2.5 μl of stock solution B)+30 μl of poly-(Glu4Tyr) stock solution C+1.21 ml of substrate solvent), 10 μl of inhibitor solution (substances corresponding to the dilutions, 3% DMSO in substrate solvent as a control) and 10 μl of enzyme solution (11.25 μg of enzyme stock solution (KDR or FLT-1 kinase) are added at 4° C. in 1.25 ml of enzyme solution (dilute). It is thoroughly mixed and incubated for 10 minutes at room temperature. Then, 10 μl of stop solution (250 mol of EDTA, pH 7.0) is added, mixed, and 10 μl of the solution is transferred to a P 81 phosphocellulose filter. Then, it is washed several times in 0.1 M phosphoric acid. The filter paper is dried, coated with Meltilex and measured in a microbeta counter.

The IC50 values are determined from the inhibitor concentration, which is necessary to inhibit the phosphate incorporation to 50% of the uninhibited incorporation after removal of the blank reading (EDTA-stopped reaction).

The results of the kinase inhibition IC50 in μM are presented in the table below:

| Example No. | VEGFR II (KDR) [μM] |
|---|---|
| 1 | 0.01 |
| 2 | 0.05 |
| 3 | 0.05 |
| 4 | 0.3 |

-continued

| Example No. | VEGFR II (KDR) [µM] |
|---|---|
| 5 | 0.3 |
| 6 | 0.3 |
| 10 | 0.2 |
| 11 | 0.2 |
| 12 | 0.7 |
| 13 | 0.2 |
| 14 | 0.2 |
| 15 | 0.2 |
| 16 | 0.1 |
| 18 | 0.02 |

Sample Application 2

Cytochrome P450 Inhibition

The Cytochrome P450 inhibition was performed according to the publication of Crespi et al. (Anal. Biochem., 248, 188-190 (1997)) with use of baculovirus/insect cell-expressed, human Cytochrome P 450 isoenzymes (1A2, 2C9, 2C19, 2D6, 3A4).

The results are presented in the following table.

| Inhibition of the Cytochrome P450 Isoenzymes (IC50, µM) | | | | | |
|---|---|---|---|---|---|
| Cytochrome P450 Isoenzyme | 1A2 | 2C9 | 2C19 | 2D6 | 3A4 |
| Example 2.54 of WO 00/27819 | 5.2 | 0.2 | 0.05 | >30 | 3.6 |
| Example 1 | >30 | 1.2 | 1.8 | >30 | >30 |

The superior action of the compounds according to the invention compared to the known compounds can be seen clearly from the result.

What is claimed is:

1. A compound formula I in which

A stands for the group —N($R^7$)—,

W stands for oxygen, sulfur, two hydrogen atoms or the group —N($R^8$)—,

Z stands for a bond, the group —N($R^{10}$)— or =N—, for branched or unbranched $C_1$-$C_{12}$-alkyl or for the group m, n and o stand for 0-3, $R_a$, $R_b$, $R_c$, $R_d$, $R_e$, $R_f$ independently of one another, stand for hydrogen, fluorine, $C_1$-$C_4$-alkyl or the group —N($R^{11}$)—, and/or $R_a$ and/or $R_b$ can form a bond with $R_c$ and/or $R_d$ or $R_c$ can form a bond with $R_e$ and/or $R_f$ or up to two of radicals $R_a$-$R_f$ can close a bridge with up to 3 C atoms each to form $R^1$ or to form $R^7$, X stands for $C_1$-$C_6$-alkyl, $R^1$ stands for branched or unbranched $C_1$-$C_{12}$-alkyl or $C_2$-$C_{12}$-alkenyl that is optionally substituted in one or more places in the same way or differently with halogen, hydroxy, $C_1$-$C_6$-alkyloxy, aralkyloxy, $C_1$-$C_6$-alkyl and/or with the group —$NR^{12}R^{13}$ or for $C_3$-$C_{10}$-cycloalkyl or $C_3$-$C_{10}$-cycloalkenyl that is optionally substituted in one or more places in the same way or differently with halogen, hydroxy, $C_1$-$C_6$-alkyloxy, $C_1$-$C_6$-alkyl and/or with the group —$NR^{12}R^{13}$ or for aryl or hetaryl that is optionally substituted in one or more places in the same way or differently with halogen, hydroxy, $C_1$-$C_6$-alkyloxy, aralkyloxy, $C_1$-$C_6$-alkyl, halo-$C_1$-$C_6$-alkyl, cyano-$C_1$-$C_6$-alkyl or with the group =O, $OR^{14}$, or $R^{14}$, $Y_1$ to $Y_5$ in each case stand for a nitrogen atom or for the group —$CY^6$, $Y_6$ stands for cyano, halogen, $C_1$-$C_6$-alkyl, $C_1$-$C_6$-alkoxy, amino or hydroxy, whereby at least one nitrogen atom is contained in the ring and at least one cyano radical is contained on the ring, D stands for a nitrogen atom or for the group C—$R^3$, E stands for a nitrogen atom or for the group C—$R^4$, F stands for a nitrogen atom or for the group C—$R^5$, G stands for a nitrogen atom or for the group C—$R^6$, whereby $R^3$, $R^4$, $R^5$ and $R^6$ stand for hydrogen, halogen, or $C_1$-$C_6$-alkoxy, $C_1$-$C_6$-alkyl or $C_1$-$C_6$-carboxyalkyl that is unsubstituted or that is optionally substituted in one or more places with halogen, $R^7$ stands for hydrogen or $C_1$-$C_6$-alkyl or forms a bridge with up to 3 ring members with $R_a$-$R_f$ from Z or to form $R^1$, $R^8$, $R^9$, $R^{10}$ and $R^{11}$ stand for hydrogen or $C_1$-$C_6$-alkyl, $R^{12}$ and $R^{13}$ stand for hydrogen, $C_1$-$C_6$-alkyl or form a ring that can contain another heteroatom, $R^{14}$ stands for the group $C_1$-$C_{15}$-alkyl-$R^{15}$, in which the alkyl radical can be interrupted in one or more places by oxygen or for the group $(CH_2—CH_2—O)_u(CH_2)_v$—$R^{15}$, $R^{15}$ stands for aryl, hetaryl, $C_1$-$C_6$-alkyl, aralkyl, —$CH_2CN$ or for the group $NR^{16}R^{17}$, $R_{16}$ and $R_{17}$ stand for hydrogen, $C_1$-$C_6$-alkyl, $C_1$-$C_6$-acyl or form a ring that can contain another heteroatom, and u and v stand for 0-5, or an isomer, enantiomer or a salt thereof.

2. A compound according to claim 1, in which

A stands for the group —N($R^7$)—,

W stands for oxygen,

Z stands for a bond or for branched or unbranched $C_1$-$C_{12}$-alkyl,

X stands for $C_1$-$C_6$-alkyl, $R^1$ stands for branched or unbranched $C_1$-$C_{12}$-alkyl or $C_2$-$C_{12}$-alkenyl that is optionally substituted in one or more places in the same way or differently with halogen, hydroxy, $C_1$-$C_6$-alkyloxy, aralkyloxy, $C_1$-$C_6$-alkyl and/or with the group —$NR^{12}R^{13}$; or for $C_3$-$C_{10}$-cycloalkyl or $C_3$-$C_{10}$-cycloalkenyl that is optionally substituted in one or more places in the same way or differently with halogen, hydroxy, $C_1$-$C_6$-alkyloxy, $C_1$-$C_6$-alkyl and/or with the group —NR$^{12}$R$^{13}$; or for aryl or hetaryl that is optionally substituted in one or more places in the same way or differently with halogen, hydroxy, C$_1$-C$_6$-alkyloxy, aralkyloxy, C$_1$-C$_6$-alkyl, halo-C$_1$-C$_6$-alkyl, cyano-C$_1$-C$_6$-alkyl or with the group =O, OR$^{14}$, or R$^{14}$, Y$_1$ to Y$_5$ in each case stand for a nitrogen atom or for the group —CY$^6$, Y$^6$ stands for cyano, halogen, C$_1$-C$_6$-alkyl, C$_1$-C$_6$-alkoxy, amino or hydroxy, whereby at least one nitrogen atom is contained in the ring and at least one cyano radical is contained on the ring, D stands for a nitrogen atom or for the group C—R$^3$, E stands for a nitrogen atom or for the group C—R$^4$, F stands for a nitrogen atom or for the group C—R$^5$, G stands for a nitrogen atom or for the group C—R$^6$, whereby R$^3$, R$^4$, R$^5$ and R$^6$ stand for hydrogen, halogen or C$_1$-C$_6$-alkoxy, C$_1$-C$_6$-alkyl or C$_1$-C$_6$-carboxyalkyl that is unsubstituted or that is optionally substituted in one or more places with halogen, R$^7$ stands for hydrogen or C$_1$-C$_6$-alkyl, or forms a bridge with up to 3 ring members with R$_a$R$_f$ from Z or to form R$^1$, R$^9$ stands for hydrogen or C$_1$-C$_6$-alkyl, R$^{12}$ and R$^{13}$ stand for hydrogen, C$_1$-C$_6$-alkyl or form a ring that can contain another heteroatom, R$^{14}$ stands for the group (CH$_2$—CH$_2$—O)$_u$(CH$_2$)$_v$—R$^{15}$, R$^{15}$ stands for aryl, hetaryl, C$_{1-6}$-alkyl, aralkyl, —CH$_2$CN or for the group NR$^{16}$R$^{17}$, R$^{16}$ and R$^{17}$ stand for hydrogen, C$_1$-C$_6$-alkyl, C$_1$-C$_6$-acyl or form a ring that can contain another heteroatom, u and v stand for 0-5, or an isomer, enantiomer or a salt thereof.

3. A compound according to claim 1, in which

A stands for the group —N(R$^7$)—,

W stands for oxygen,

Z stands for a bond or for branched or unbranched C$_1$-C$_{12}$-alkyl,

X stands for C$_1$-C$_6$-alkyl,

R$^1$ stands for aryl or hetaryl that is optionally substituted in one or more places in the same way or differently with halogen, hydroxy, C$_1$-C$_6$-alkyloxy, aralkyloxy, C$_1$-C$_6$-alkyl, halo-C$_1$-C$_6$-alkyl, cyano-C$_1$-C$_6$-alkyl or with the group =O, —OR$^{14}$, or R$^{14}$, Y$_1$ to Y$_5$ together stand for a pyridyl ring, which is substituted with a cyano group and which can be substituted in addition with halogen, C$_1$-C$_6$-alkyl, C$_1$-C$_6$-alkoxy, amino, C$_1$-C$_6$-carboxyalkylamino or hydroxy, D stands for a nitrogen atom or for the group C—R$^3$, E stands for a nitrogen atom or for the group C—R$^4$, F stands for a nitrogen atom or for the group C—R$^5$, G stands for a nitrogen atom or for the group C—R$^6$, whereby R$^3$, R$^4$, R$^5$ and R$^6$ stand for hydrogen, halogen, or C$_1$-C$_6$-alkoxy, C$_1$-C$_6$-alkyl or C$_1$-C$_6$-carboxyalkyl that is unsubstituted or that is optionally substituted in one or more places with halogen, R$^7$ stands for hydrogen or C$_1$-C$_6$-alkyl, or forms a bridge with up to 3 ring members with R$_a$-R$^f$ from Z or to form R$^1$, R$^9$ stands for hydrogen or C$_1$-C$_{6-alkyl}$, R$^{14}$ stands for the group (CH$_2$—CH$_2$—O)$_u$(CH$_2$)$_v$—R$^{15}$, R$^{15}$ stands for aryl, hetaryl, C$_{1-6}$-alkyl, aralkyl, —CH$_2$CN or for the group NR$^{16}$R$^{17}$, R$^{16}$ and R$^{17}$ stand for hydrogen, C$_1$-C$_6$-alkyl, C$_1$-C$_6$-acyl or form a ring that can contain another heteroatom, u and v stand for 0-5, or an isomer, enantiomer or a salt thereof.

4. A compound according to claim 1, in which

A stands for the group —N(R$^7$)—,

W stands for oxygen,

Z stands for a bond or C$_1$-C$_6$-alkyl,

X stands for C$_1$-C$_6$-alkyl,

R$^1$ stands for thiophene, furan, oxazole, thiazole, indazolyl, imidazole, pyrazole, pyridine, pyrimidine, triazine, quinoline, isoquinoline or

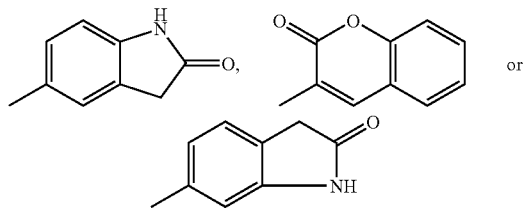

that is optionally substituted in one or more places in the same way or differently with halogen, hydroxy, C$_1$-C$_6$-alkyloxy, aralkyloxy, C$_1$-C$_6$-alkyl, halo-C$_1$-C$_6$-alkyl, cyano-C$_1$-C$_6$-alkyl or with the group =O, Y$_1$ to Y$_5$ together stand for a pyridyl ring, which is substituted with a cyano group and which in addition can be substituted with halogen, D stands for a nitrogen atom or for the group C—R$^3$, E stands for the group C—R$^4$, F stands for the group C—R$^5$, G stands for the group C—R$^6$, whereby R$^3$, R$^4$, R$^5$ and R$^6$ stand for hydrogen, R$^7$ stands for hydrogen, and R$^9$ stands for hydrogen, or an isomer, enantiomer or a salt thereof.

5. A compound according to claim 1, in which

A stands for the group —N(R$^7$)—,

W stands for oxygen,

Z stands for a bond,

X stands for C$_1$-C$_6$-alkyl,

R$^1$ stands for indazolyl, quinoline, isoquinoline or

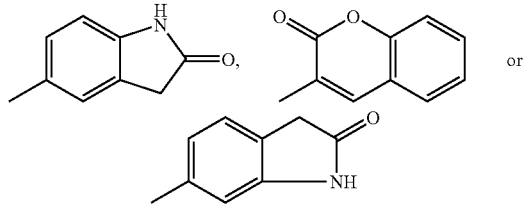

that is optionally substituted in one or more places in the same way or differently with C$_1$-C$_6$-alkyloxy, C$_1$-C$_6$-alkyl, cyano-C$_1$-C$_6$-alkyl or with the group =O, Y$_1$ to Y$_5$ together stand for a pyridyl ring, which is substituted with a cyano group and which in addition can be substituted with halogen, D stands for a nitrogen atom or for the group C—R$^3$, B stands for the group C—R$^4$, F stands for the group C—R$^5$, C stands for the group C—R$^6$, whereby R$^3$, R$^4$, R$^5$ and R$^6$ stand for hydrogen, R$^7$ stands for hydrogen, and R$^9$ stands for hydrogen, as well as isomers, enantiomers and salts thereof.

6. A pharmaceutical agent containing a pharmaceutically acceptable carrier and at least one compound according to claim 1.

7. A method of treating psoriasis, Kaposi's sarcoma, restenosis, endometriosis, Crohn's disease, Hodgkin's disease, leukemia; arthritis, rheumatoid arthritis, hemangioma, angiofibroma; eye disease, diabetic retinopathy, neovascular glaucoma; renal disease, glomerulonephritis, diabetic nephropathy, malignant nephrosclerosis, thrombic microangiopathic syndrome, transplant rejection, glomerulopathy; fibrotic disease, cirrhosis of the liver, mesangial cell proliferative disease, arteriosclerosis, injury to nerve tissue comprising administering a therapeutically effective amount of a pharmaceutical agent according to claim 6.

8. A compound according to claim 6 with suitable formulation substances and vehicles.

9. A pharmceutical agent according to claim 6 in the form of a pharmaceutical preparation that is suitable for enteral, parenteral or oral administration.

10. A method for treating psoriasis, Kaposi's sarcoma, restenosis, endometriosis, Crohn's disease, Hodgkin's disease, leukemia; arthritis, hemangioma, angiofibroma; eye disease, neovascular glaucoma; renal disease, diabetic nephropathy, malignant nephrosclerosis, thrombic microangiopathic syndrome, transplant rejection, glomerulopathy; fibrotic disease, mesangial cell proliferative disease, arteriosclerosis or injury to nerve tissue comprising administering an inhibitory amount of a compound according to claim 1.

* * * * *